US006753186B2

(12) United States Patent
Moskoff

(10) Patent No.: US 6,753,186 B2
(45) Date of Patent: Jun. 22, 2004

(54) WATER QUALITY MONITORING AND TRANSMISSION SYSTEM AND METHOD

(75) Inventor: Harold I. Moskoff, Ontario (CA)

(73) Assignee: eWaterTek Inc., Ontario (CA)

( * ) Notice: Subject to any disclaimer, the term of this patent is extended or adjusted under 35 U.S.C. 154(b) by 0 days.

(21) Appl. No.: 10/097,855

(22) Filed: Mar. 15, 2002

(65) Prior Publication Data
US 2002/0130069 A1 Sep. 19, 2002

Related U.S. Application Data
(60) Provisional application No. 60/276,038, filed on Mar. 16, 2001.

(51) Int. Cl.[7] ............................................. G01N 21/33
(52) U.S. Cl. ............................ 436/125; 4/638; 210/94; 250/493.1; 422/82.05; 422/119; 436/164; 73/863.01
(58) Field of Search .......................... 4/638; 422/82.05, 422/82.09, 50, 68.1, 81, 119; 436/164, 39, 125, 161; 250/493.1; 210/85, 94, 96.1, 143, 192, 198.2, 739, 748, 656, 920, 424, 433, 449; 73/53.01, 61.41, 61.43, 64.85, 863, 863.01, 863.21, 863.31; 700/266; 702/22, 23, 25, 31, 32, 50; 705/1

(56) References Cited

U.S. PATENT DOCUMENTS

| | | | |
|---|---|---|---|
| 5,191,613 A | | 3/1993 | Graziano et al. |
| 5,494,573 A | | 2/1996 | Schoenmeyr et al. .......... 210/94 |
| 5,646,863 A | * | 7/1997 | Morton ......................... 210/85 |
| 5,654,201 A | | 8/1997 | Capuano ..................... 436/125 |
| 5,865,991 A | | 2/1999 | Hsu ............................. 340/609 |
| 5,892,690 A | | 4/1999 | Boatman et al. |
| 6,021,664 A | | 2/2000 | Granato et al. ............. 73/53.01 |
| 6,024,867 A | | 2/2000 | Parise |
| 6,106,705 A | * | 8/2000 | Giordano et al. ........... 210/449 |
| 6,245,224 B1 | * | 6/2001 | Enoki et al. ................ 210/96.1 |
| 6,290,908 B1 | * | 9/2001 | Fukunaga et al. ............. 210/85 |
| 6,356,205 B1 | * | 3/2002 | Salvo et al. ................. 210/143 |
| 6,491,828 B1 | * | 12/2002 | Sivavec et al. ................ 210/85 |

FOREIGN PATENT DOCUMENTS

| | | |
|---|---|---|
| WO | 00/75898 | 12/2000 |
| WO | 01/94937 | 12/2001 |

* cited by examiner

*Primary Examiner*—Joseph W. Drodge
(74) *Attorney, Agent, or Firm*—Jacobson Holman PLLC

(57) ABSTRACT

A water quality sampling system and method in which compact water impurity detector and monitoring units intended for domestic use are installed in a residential environment while detected values are electronically transmitted to a Central Monitoring Station (CMS), where customers can register and pay over the Internet. Using the impurity detector units, a portion of an incoming water stream is passed to an analyzer for detection of chlorine and various contaminants. The detector analyzes related data for determining the condition and extent of impurity in the water elements. This data is transmitted from a compact control box, known as the wall unit, that translates the data for output to the CMS, located in another geographic locale, via a common data acquisition network. This network can be the Internet or a cellular and/or satellite connection. Upon detection of contaminants above a threshold level, the monitoring device will make a sound through a wall unit located in the vicinity, to warn the average household tap water user of such unsatisfactory condition of his/her water elements, as the conditional values are sent using EDI onto the network, and then onward to the CMS website.

42 Claims, 10 Drawing Sheets

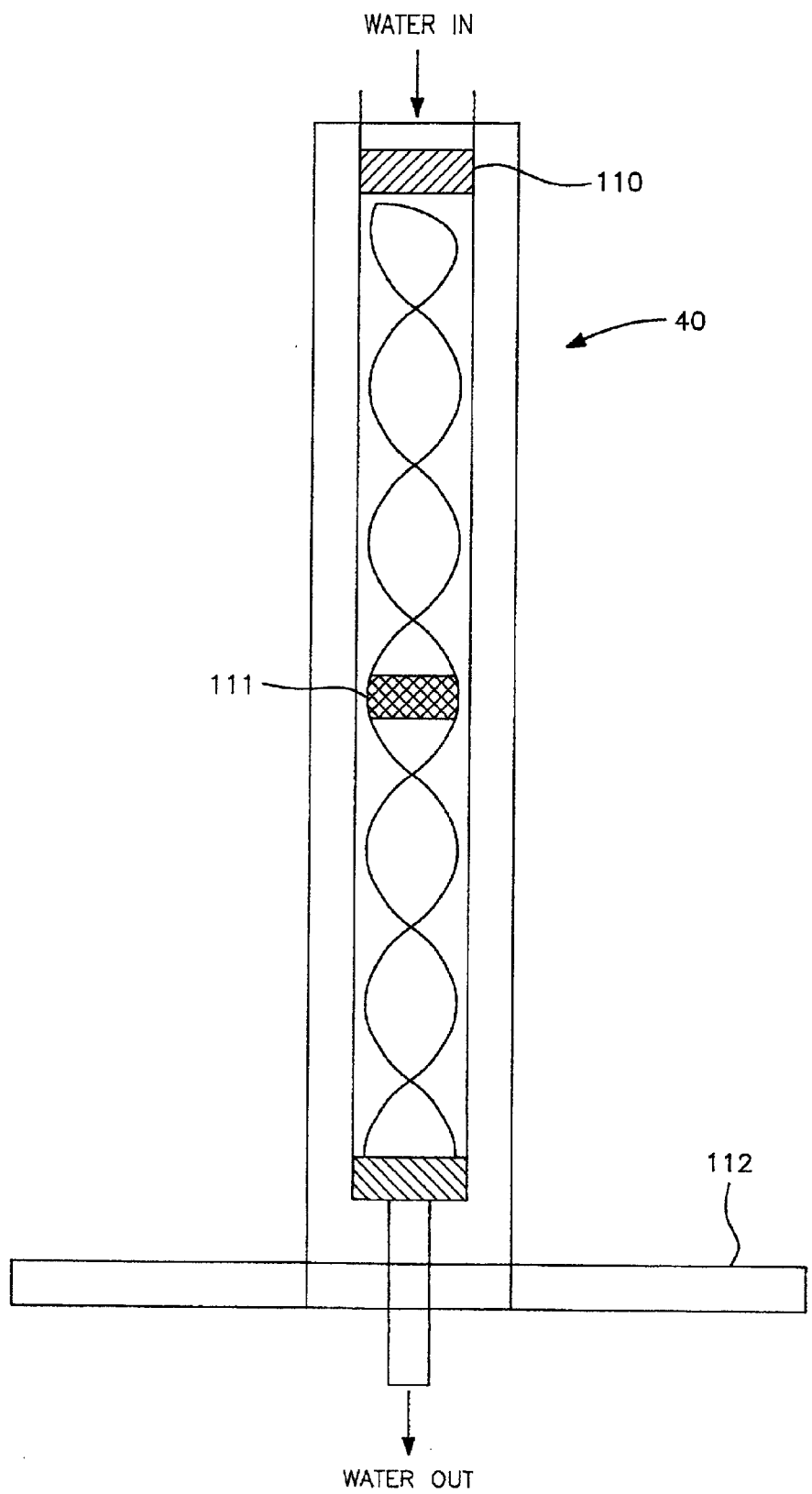

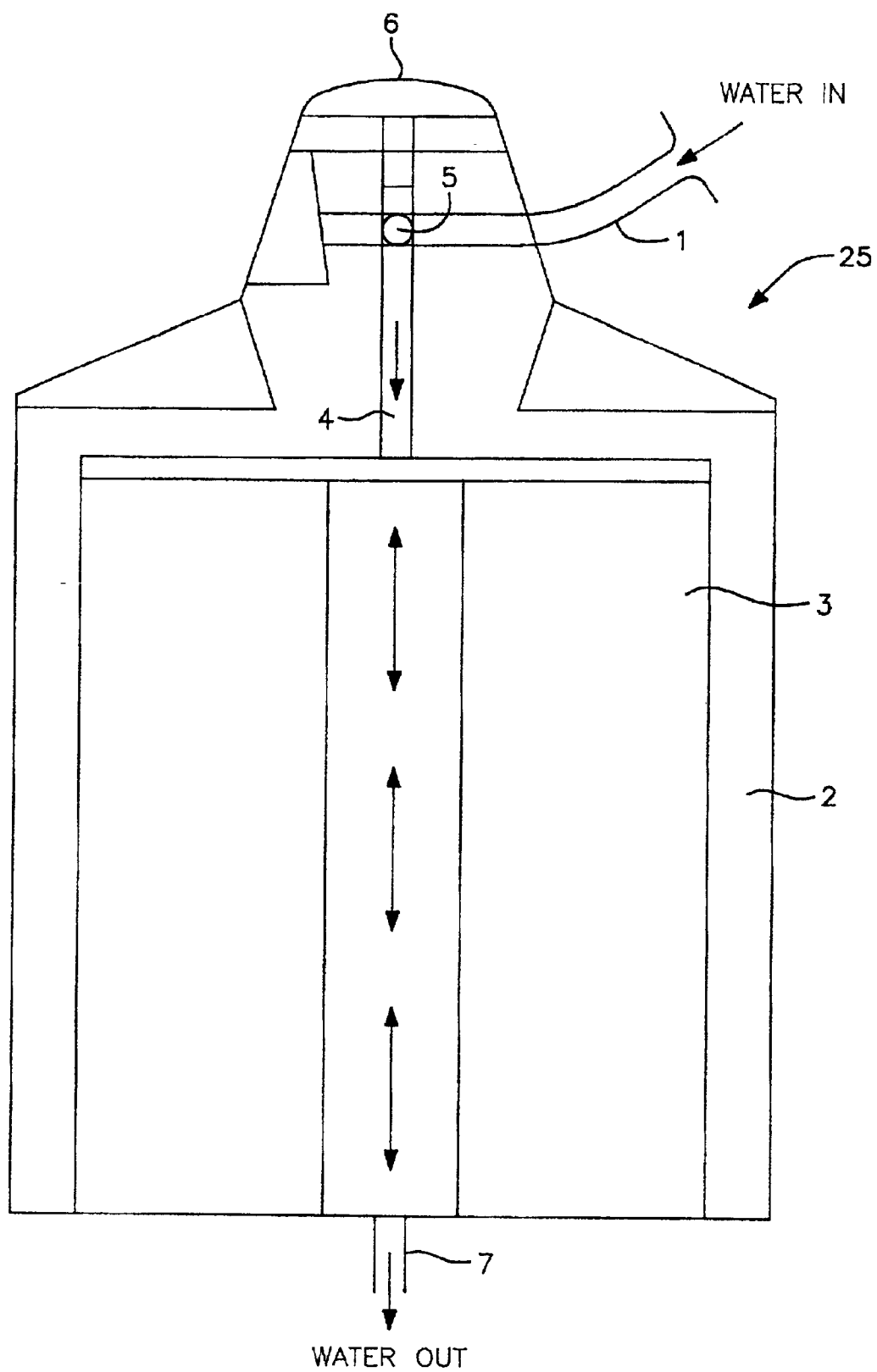

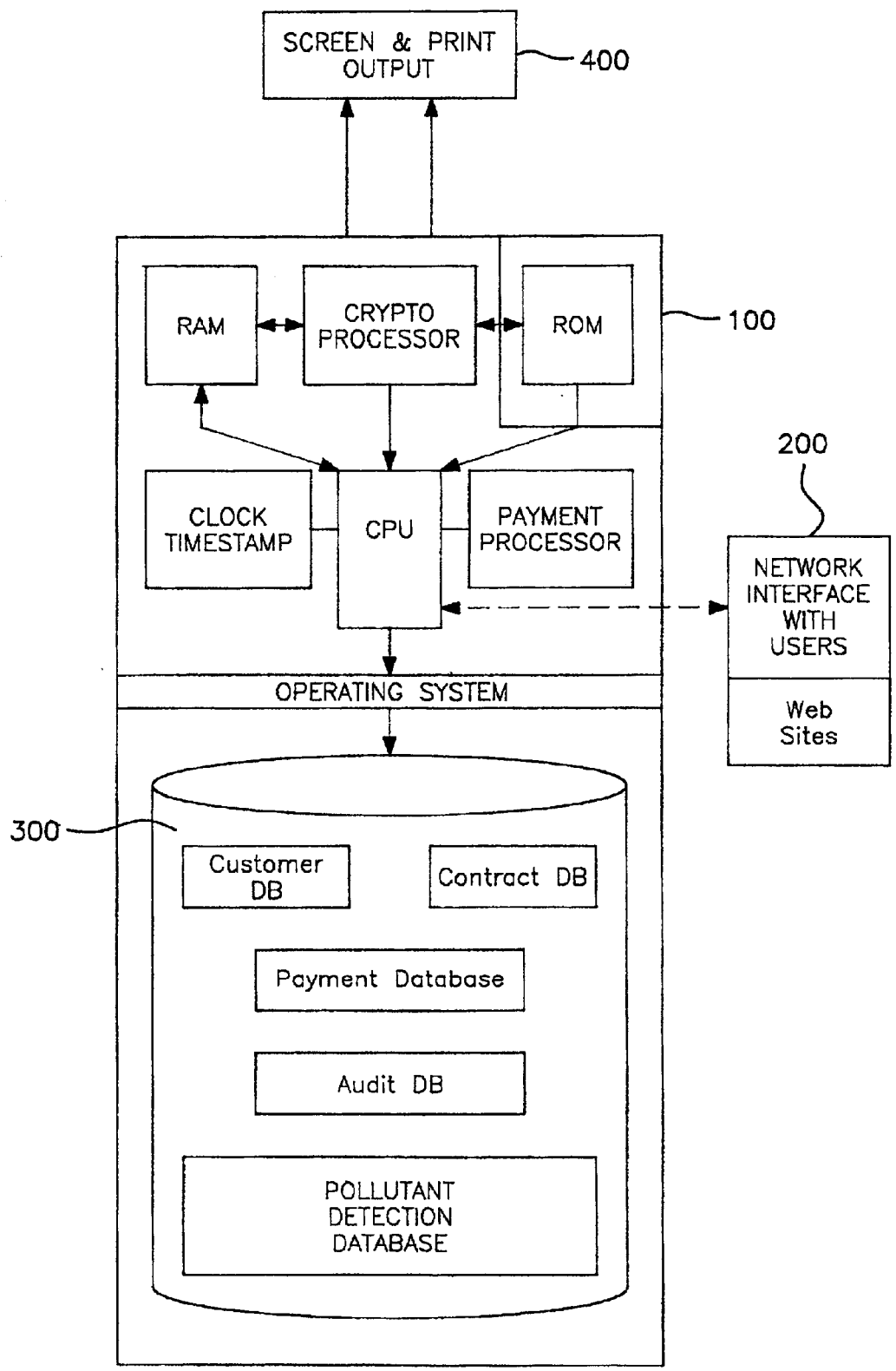

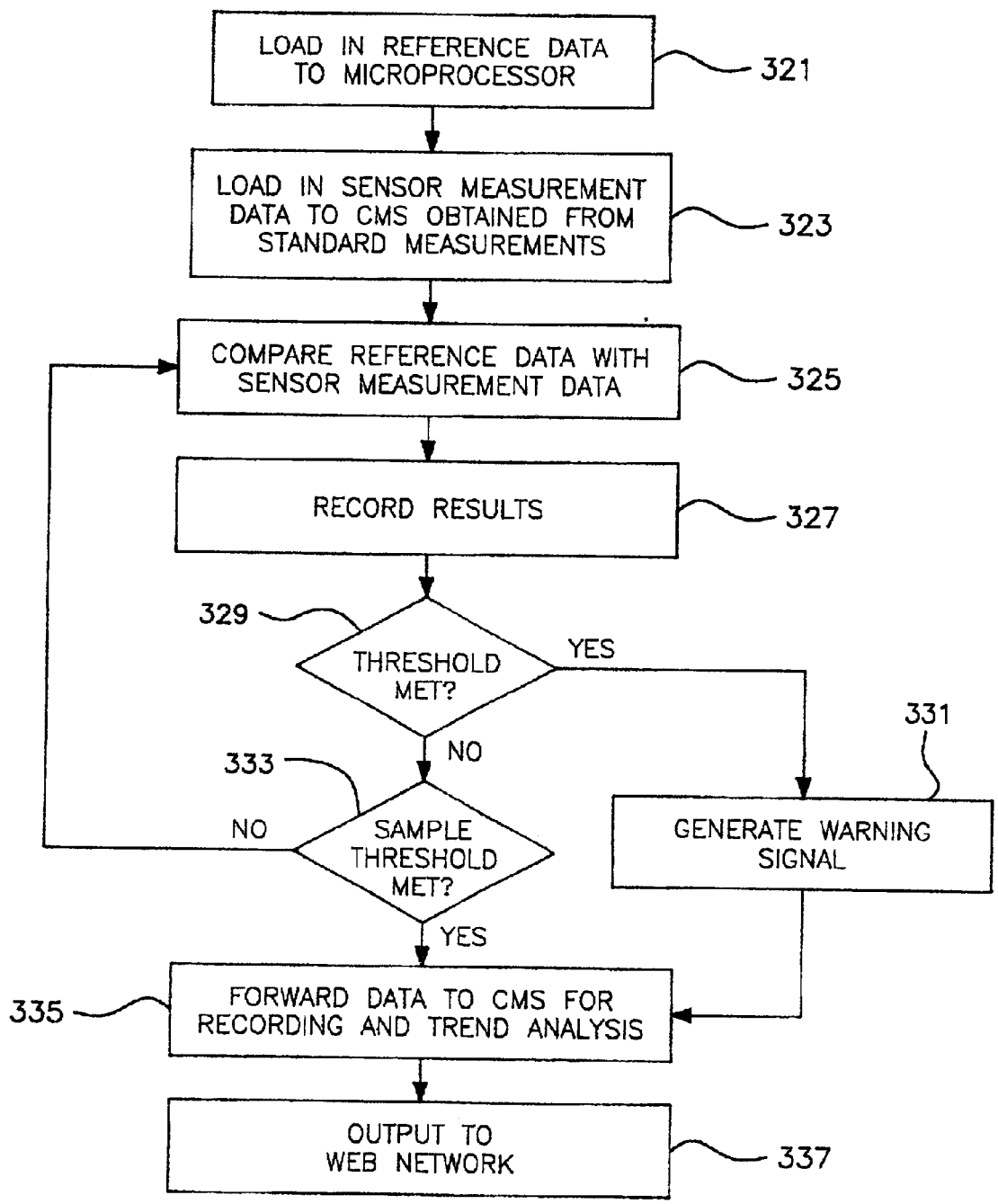

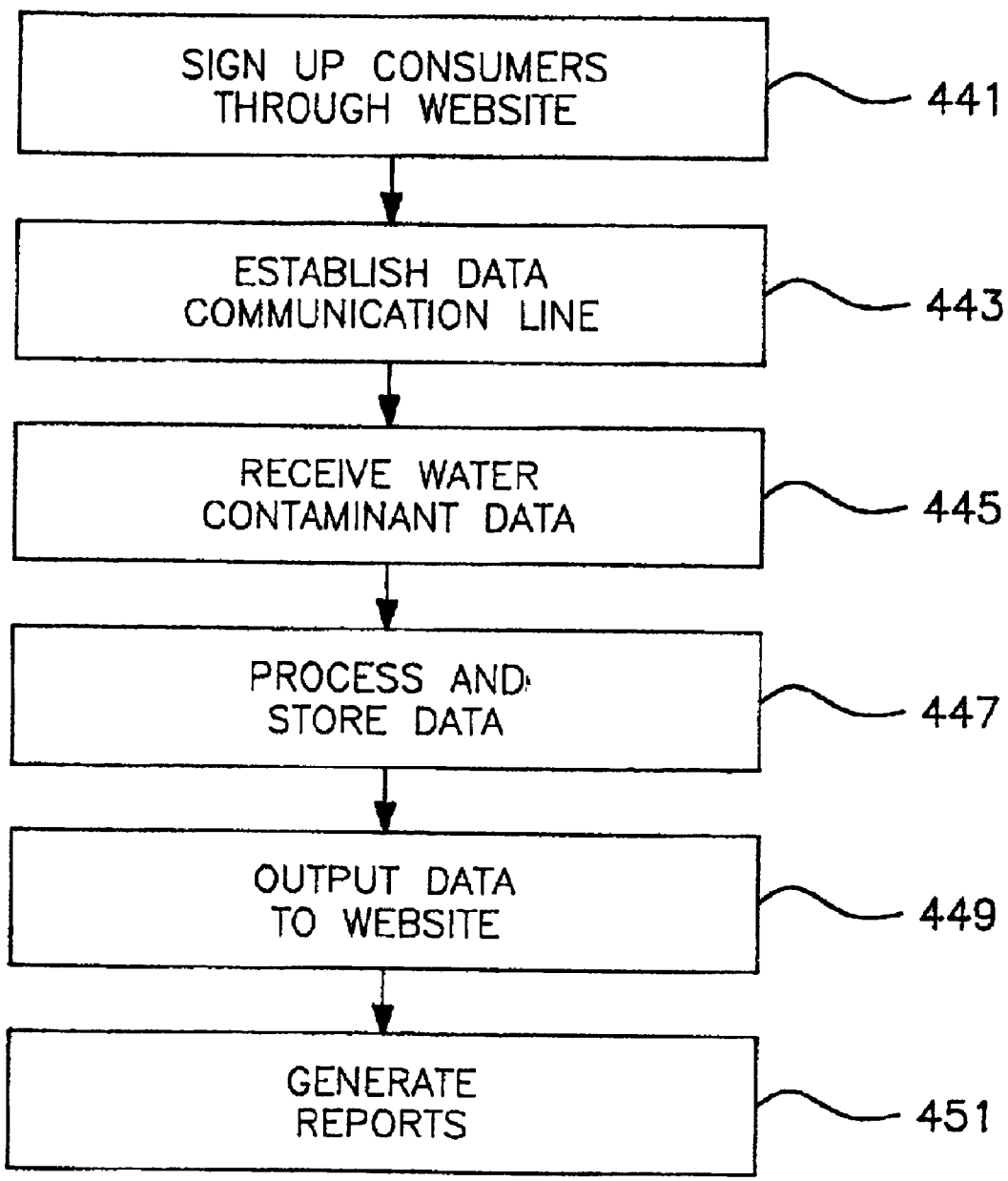

WATER QUALITY MONITORING AND TRANSMISSION SYSTEM AND METHOD

This invention is entitled to the benefit of, and claims priority from, U.S. provisional application Serial No. 60/276,038 with filing date of Mar. 16, 2001.

BACKGROUND OF THE INVENTION

1. Field of the Invention

This invention relates generally to water monitoring systems and, more particularly, to a system and method for monitoring the quality of tap water using a drinking water impurity detection system that simultaneously transmits and records water quality data, with interactive web-interface to facilitate user sign-up processes.

2. Description of the Prior Art

The demand for purer water products is generally increasing. Government agencies need to produce higher quality water products, of the kind derived using chlorine in particular, in order to meet increasingly stringent safety and environmental standards, as well as to improve general operations. Additionally, due to the demand for purer tap water by its millions of household users worldwide, public health authorities are being increasingly compelled to monitor the various contaminants in the water stream during the various processes such as, for example, desalination, to ensure that the water meets the demand for purity and to be able to take rapid corrective measures to detect and/or reduce the contaminants when they do begin to appear. Particular contaminants, which may be present in the water and more particularly, in the chlorine content, are halocarbons, including methylene chloride, chloroform. (U.S. Pat. No. 5,654,201 discloses a representative chlorine quality monitoring system.) In order to monitor the water contaminants and have the ability to take corrective action, it is necessary that a suitable system and method be available which will accurately detect and measure such contaminants and which can also be used on-line at the household site, taking samples directly from its tap stream.

The primary causes of water pollution include household waste, industrial waste, farm pesticide(s) and the animal waste produced by hog and poultry farms which can result in the notorious *E. coli* strain of bacteria, responsible for a number of recent fatalities. As the pollution problems threatening the source of our drinking water such as the river become increasingly worrisome, people lose their confidence in the quality of the drinking water provided by the local water company and/or government ministries. In addition, people's anxiety about the quality of their drinking water is further aggravated by the fact that the conditions of the water supplying pipes and reservoirs are often found to be unsatisfactory. Accordingly, a variety of water-treating devices such as water-filtering devices, water purifying devices, water softening devices, etc., have become ubiquitous in offices, homes, factories, schools, religious institutions and so on.

The conventional systems for water purification have now become passé, creating the requirement for a new detection device and system, as opposed to a filter, that will serve this need to warn the average household user of a potential health hazard not only in the household, but quite possibly and much more probably, in the community at large. Existing systems, such as that shown in U.S. Pat. No. 5,865,991, can be used to warn individual consumers but fail to integrate water quality information from a plurality of consumers; such integration not only helps to identify the overall scope of an existing water contamination problem but also enables consumers to be pre-warned of potential problems through notification of surrounding water quality readings.

Even in the case of the average carbon or reverse-osmosis filters that are currently on the market, the purifying elements used there are generally replaced after a predetermined period of time of usage without knowing the actual condition of the elements themselves. For example, U.S. Pat. No. 6,024,867 discloses a water filter that displays the state of the life span of a filter cartridge therein, based on the amount of water which has passed through the filter. This approach assumes a relatively constant contaminant level in the incoming water and does not account for actual contamination which may increase in response to environmental or other changes. Hence, in many cases, overused purifying elements are not replaced in a timely manner, thus resulting in the consumer unknowingly drinking the poor quality water produced by such an ineffective water purification system. This scenario actually provides an excellent environment for bacteria and fungi to grow. Such overused and clogged elements would contaminate the water passing through the systems instead of purifying it. This illustrates the need not only for a filtration element, but more importantly perhaps, an impurity and contaminant identifier.

Representatively, U.S. Pat. No. 5,646,863 is directed to the detection of contaminants in water supplies of municipal utilities, industrial processes and surrounding water supply systems. Ground, surface or industrial water is pumped into a storage chamber and preconditioned for analysis. The water analysis structure is highly complex, including such elements as hydraulic module, fuzzy logic correlator and controller, neural network, etc., and does not represent a system that may be easily and effectively implemented within the household environment of a typical consumer for immediate tap water quality verification and which enables the consumer to receive feedback through a centralized monitoring station over a distributed computer network.

U.S. Pat. No. 5,494,573 teaches a water purification monitoring system for a beverage processing system. Various system characteristics are monitored using sensors, with data being transmitted to a remotely located computer for diagnosis. The system is designed to operate at the municipal water supply level for monitoring a primary water source, and is not a practical solution for residential water quality monitoring requirements on an individualized basis.

Previously, a common practice in home water monitoring has been to send an individual sample of water to be tested by way of a water-sampling laboratory, litmus tests, etc. It has become important, however, for public health bacteriologists to have a faster, more accurate way of measuring certain selected characteristics possessed by a single simple sample of common tap water. In addition, it is important to note that a single sample is of limited value. The most a single sample can show is the water quality at the time and place of sampling. Therefore, a system is needed whereby repeat samplings may be performed, such as every few weeks.

Whether one sample or many, the whole process generally needs to be expedited from a customer's standpoint. Having an electronic file transfer of information pertaining to the above allows costs to be kept to a minimum. Although the traditional paper contract serves the purpose of security well, nowadays authentication systems have been developed specifically to ensure the enforceability of electronic contracts, as mentioned later in this document. One such method of authenticating electronic contracts in order to make them legally enforceable is disclosed in U.S. Pat. No. 5,191,613, which utilizes digital signatures.

There exists therefore, a significant need for further improvements: 1) in expediting the whole water monitoring process on an individual basis; 2) in water quality monitors for testing and indicating the relative quality of a tap water system, particularly a water quality monitor made responsive to the predetermined values of the unit so that accurate and reliable test readings will result in a more spontaneous fashion; 3) in regularly repeating the water sampling process in a convenient, cost-effective way; and 4) in integrating water quality data from a plurality of consumers through the means of today's available technology to transmit information across vast distances, if necessary, to a Central Monitoring Station (CMS) through which customer feedback information is provided over a distributed computer network.

SUMMARY OF THE INVENTION

In light of the above, the primary object of the present invention is to provide an improved system and method for measuring chlorine and contaminants in tap water which allows for quickened response and recording for the user, measuring a plurality of different contaminants.

Another object of the invention is to disclose a novel apparatus for automatically making intermittent qualitative measurements of the properties of a water sample, in order to determine if the water meets certain predescribed standards as programmed, and then advancing informational values to the Central Monitoring Station (CMS) when the output water quality is below that standard.

It is another related object of the present invention to provide a water analyzing system of the aforementioned type which is particularly useful in determining if industrial water being drawn from a pipe is in a suitable unpolluted condition for an average household consumer.

It is yet another object to disclose an apparatus that can sense and sequentially record (on a single screen) a heavy metal level or other component content of a flowing sample of tap water, for example, a chlorine content, such that the user can always be assured that he/she has a reliable computer-charted representation of his or her water stream available within moments over a distributed computer network.

Another object of the invention is a technique for repeatedly testing water samples at a consumer's tap which allows for valid comparison of data collected in different places at various times and identification of trends in water quality.

A further object of the invention is a method for using a computer system to facilitate a transaction between a customer and a company, comprising inputting into the computer a payment identification specifying a credit card account and simultaneously being automatically assigned a password unique to that customer, for sign-up to the water monitoring service and corresponding website of the present invention.

Yet another object of the invention is an integrated water monitoring and reporting system in which water quality data is collected from a plurality of consumers by a CMS and made available to the consumers on a web site accessible over a distributed computer network such as the Internet.

These and other objects and advantages of the present invention may be achieved through the provision of a system and method of sensing the presence of various contaminants, chlorine, heavy metals, etc., in tap water, and providing a warning alert signal to the user in a more immediate and improved fashion. The present invention ensures that the tap water will maintain a quality of purity in conformity with the standard in public health for that region. The present invention is also adapted for notifying off-site maintenance personnel at a CMS of a hazardous public health situation, and recording the data for future reference. An added benefit to the user is the ability to sign up for the services immediately with the ability to choose the terms via live web interaction, and of viewing their water usage as well. This system and method may also be applied to business and industrial usage.

The method for monitoring the quality of drinking water according to the present invention comprises taking a sample in a stream of water, passing a portion of the sample to an analyzer, detecting the presence of chlorine, heavy metals, etc. in the sample stream, and passing that data (via EDI) regarding the presence of the detected material to a common data acquisition network, which could be wireless, for recording and data output at CMS, and then onwards to the website for customer queries.

The present invention comprises a system and method for monitoring the quality of water and transmitting that information. A preferred embodiment includes a line for taking a sample stream of water, an analyzer, a microprocessor control box, and a common data acquisition network. Lines may be provided for taking a plurality of portions of the sample and passing portions to the analyzer. The analyzer may be a halocarbon in chlorine analyzer, a fiber-optic based residual chlorine monitor, and/or an ultra-violet lamp/reactor located beneath the faucet tap water unit or adjacent an incoming water line near the hot water heater or pump, depending on the embodiment. The control box converts the signals and transmits them onto the network. A central monitoring station is provided for receiving data from the network and integrating and outputting that data.

Through the use of a suitable number of the aforementioned described instruments, it is possible to present concrete evidence on a charted record(s) or database, located at the CMS, showing the exact time at which a certain measured condition of the tap water indicated it to be contaminated and/or polluted. These values can be presented on a corresponding website within minutes of detection.

The present invention provides rapid analysis and reliability. There is no required maintenance for photometric devices, and no chemicals are required. The system exhibits no drift in the response over time and, for spectrophotometric devices, is not affected by interferences. Furthermore, the overall system is relatively portable. These and other objects are attained by the present invention which may be better understood from the following description, reference being made to the accompanying drawings.

BRIEF DESCRIPTION OF THE SEVERAL VIEWS OF DRAWINGS

FIG. 2 illustrates a chromatographic column of the system for monitoring water quality as set forth in FIG. 1;

FIG. 3 is a drawing of a UV lamp and reactor that generates contaminant signals for use within the water monitoring system in accordance with the present invention;

FIG. 5 is a block diagram of a preferred embodiment of the central controller at the CMS in accordance with the present invention;

FIG. 9 is a flowchart setting forth the steps undertaken according to the present invention in monitoring water quality measurements over time and reporting in response to contaminant level and/or upon a number of samples threshold; and FIG. 10 is a flowchart setting forth the steps undertaken according to the present invention to establish a network of water monitoring consumers communicating through a central monitoring station.

It is to be noted however, that the appended drawings illustrate only a typical embodiment of this invention and are therefore not to be considered limiting of its scope, for the invention may admit to other equally effective embodiments. In fact, a variety of further modifications and improvements to the water quality monitoring system inherent in the present invention will be apparent. Thus, no limitation on the invention is intended in any way, shape or form in the following description and accompanying drawings, except as put forth herein.

DETAILED DESCRIPTION OF THE PREFERRED EMBODIMENTS

The present invention is directed to a compact, modular water detector and transmission system to be used by an operator. In general, the automatic water impurity detection system, transmitter and central monitoring station with corresponding website includes a detector which is suitable for use with liquids; a monitoring device; a means for translating outputted values by means of a wall unit; a common data acquisition network; and a remote monitoring station.

Figure 1:
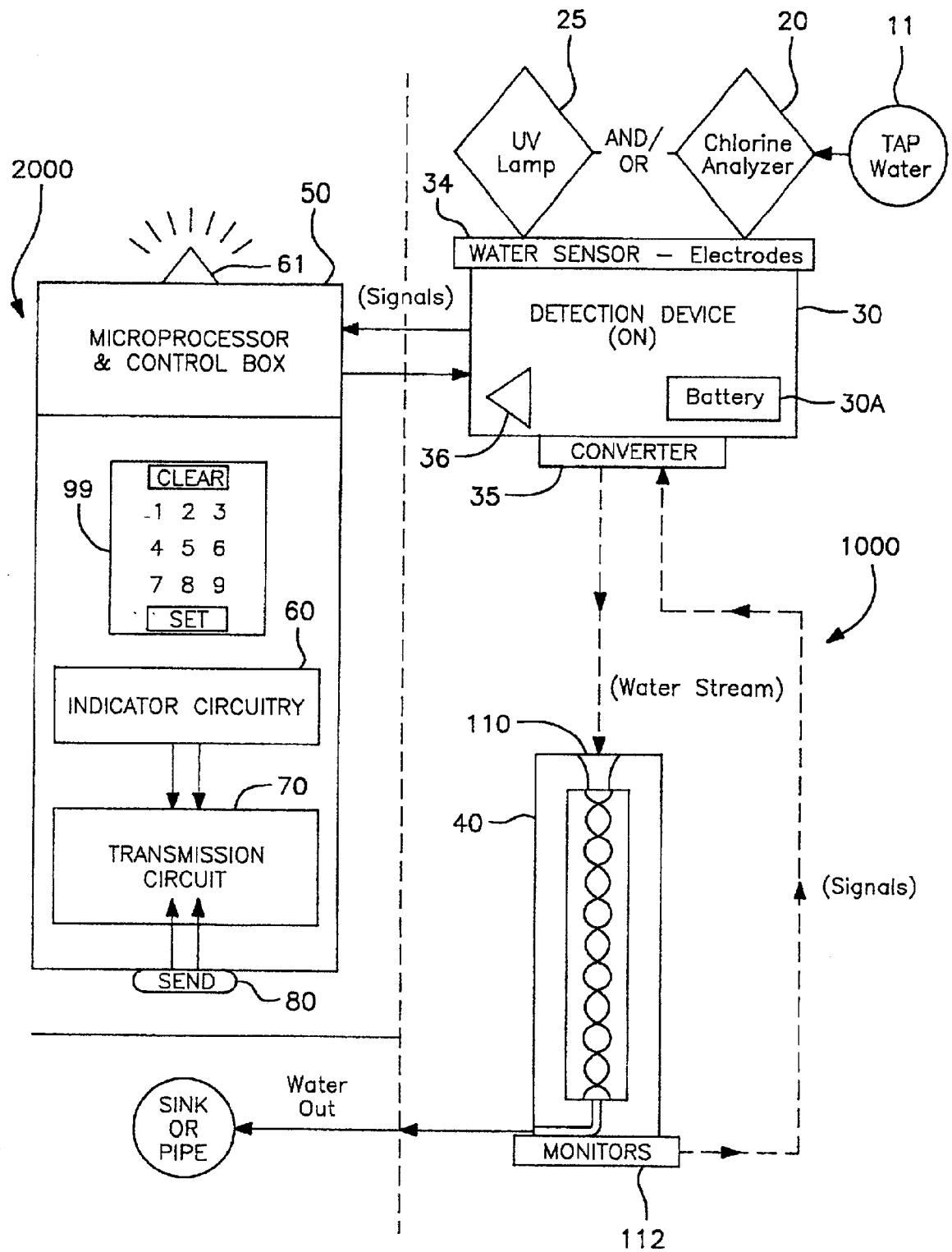
FIG. 1 is a schematic illustration of a system detecting water contamination in a general embodiment of the present invention.
Figure 6:
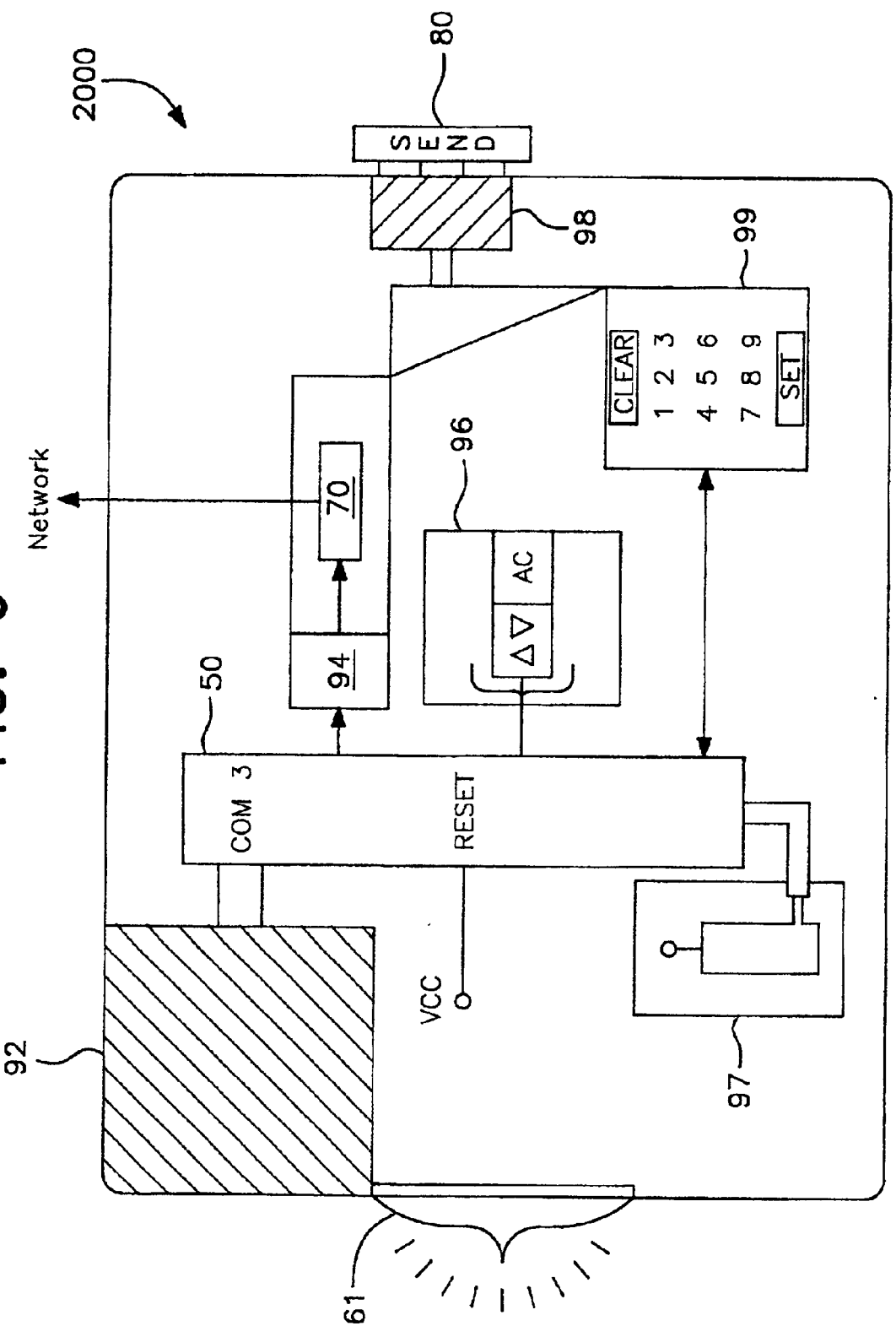
FIG. 6 is a block diagram of the monitoring device and microprocessor in the wall unit control box of FIG. 1.
Figure 7:
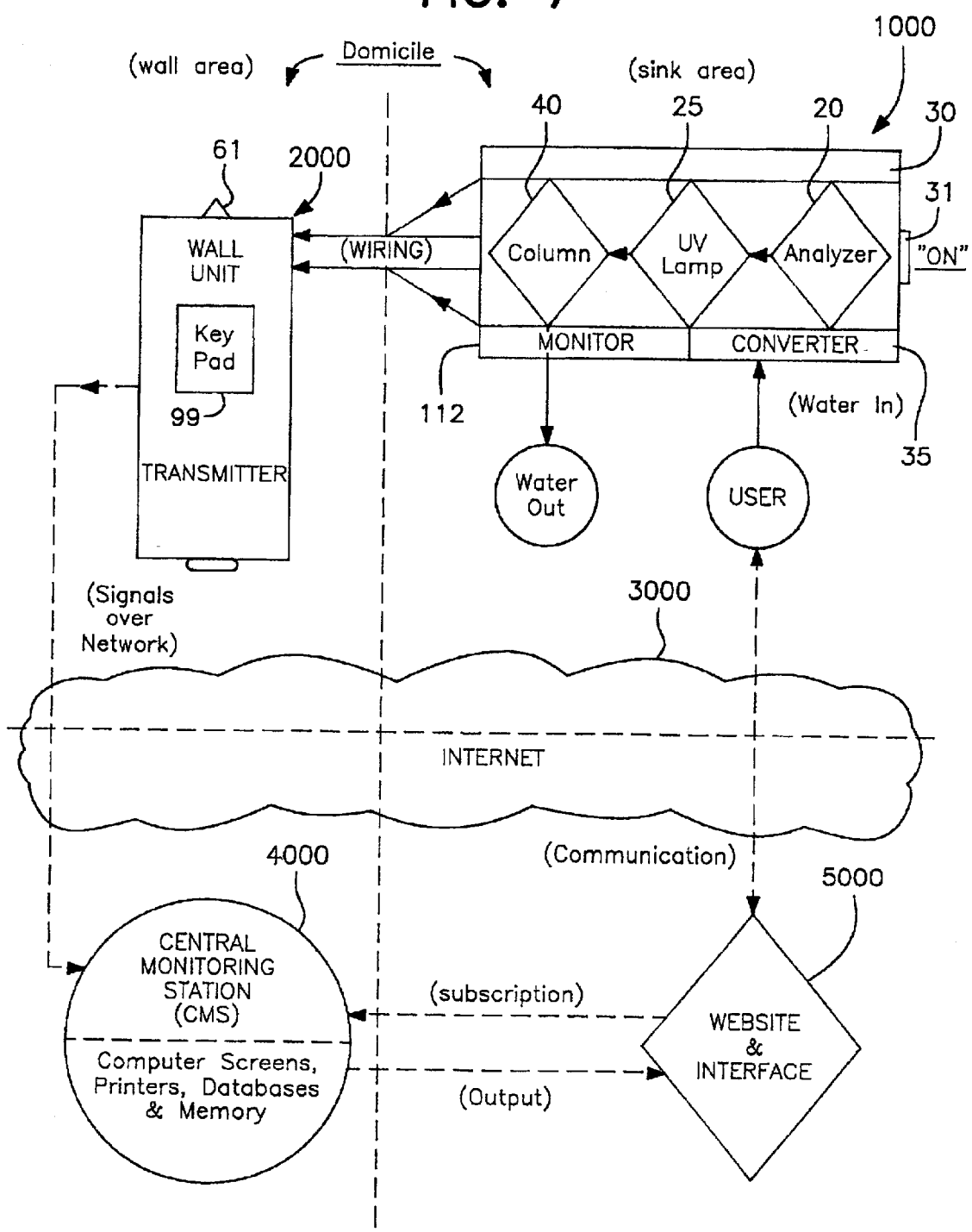
FIG. 7 is a block diagram outlining the framework and connectivity to the central monitoring station in accordance with the present invention.

Referring to the drawings, FIG. 1 illustrates the detecting unit, generally designated by the reference numeral 1000, and the microprocessor-controlled wall unit, generally designated by the reference numeral 2000, as would be used in a user's home, office or industrial/business setting. FIGS. 2 and 3 depict in greater detail the chromatographic column and ultraviolet lamp of FIG. 1, respectively. FIG. 5 is a block diagram of the central controller of the central monitoring station which receives data from the microprocessor-controlled wall unit of the user. FIG. 6 depicts in greater detail the microprocessor-controlled wall unit of FIG. 1. Finally, FIG. 7 illustrates the components of the overall water quality monitoring and transmission system and method of the present invention, including detecting unit 1000, wall-mounted monitoring unit 2000, central monitoring station 4000, and web site and interface 5000 to a distributed computer network 3000 such as the Internet, or a cellular and/or satellite connection.

More specifically, the wall-mounted monitoring unit 2000 of the present invention includes a microprocessor 50 operable for storing a first predetermined reference value which might be a minimum permissible health standard in the water sample. Indicator circuitry 60, which is electrically wired to the microprocessor, provides notification regarding current detection levels, settings and conditions sent from the detecting unit 1000; this data may include a current recorded time, and an indicator that illustrates whether the drinking water is contaminated and/or polluted and therefore not fit for consumption. The detection device 30 is electrically connected to the microprocessor 50 for monitoring a level or condition of each element to detect the quality of the drinking water made up by these elements. The detection device 30 analyzes a related condition detecting value detected for determining the condition of each of the elements. The control box is equipped with a "SEND" button 80 to initiate transmission of the data onto the network 3000. The wall unit 2000 further includes a memory 98 for storing conductivity readings. Output means, typically located at the CMS 4000 at a separate geographic locale, may include a monitor, printer, website, etc. for displaying a visual signal representative of the conductivity reading.

The detecting unit 1000, which is electrically connected to the microprocessor 50 for monitoring a qualitative condition of the tap water, comprises impurity detecting circuitry that may include at least one pure water electrode in contact with the tap water stream, and means responsive to an activation signal to deliver a test pulse wave to the pure water electrode to take a conductivity reading representative of the relative quality of the water. A battery and charging circuit, including battery 30A and power source 96, generates and delivers the activation signal to the monitor circuit and microprocessor in the wall unit. The impurity detecting circuitry within the detection device 30, which is electronically connected to the microprocessor, includes a water sensor 34, an amplifier 36, and an analog to digital voltage converter 35, all electrically connected. The water sensor 34 detects a code in the detection device 30 and generates a chlorine condition detecting value which is readable by the amplifier. A predetermined reference value is preset in the amplifier, and the condition detecting value indicates whether the water has reached the predetermined reference value. The raw signals are converted to numerical codes. A first analog signal is sent to the analog to digital voltage converter 35 for conversion to a digital signal which is transmitted to the microprocessor 50 which then activates the wall unit transmission device 70 for transmission of the signal onward, over the network 3000, to the CMS 4000. An "ON" switch 31 will be apparent on the detection device 30 in order to redirect the water stream and initiate the system to read a user-inputted impurity variable.

When the condition detecting value exceeds the predetermined reference value, a digital signal is sent out from the activated detecting circuitry of the detection device 30 to the microprocessor wall unit 2000 to activate the microprocessor 50 in order to send out an activating signal to the indicator circuitry 60 to notify users to stop drinking the tap water.

The present invention may further include information input circuitry, which may be mounted on the wall unit 2000 and electrically connected to the microprocessor, for keying predetermined reference values into the microprocessor. Such information input circuitry may comprise an input keyboard 99 which has a plurality of numeral keys from 0 to 9, a "SET" key, as well as a "CLEAR" key. Preselected values, such as chlorine values, are keyed in by pressing numerical keys, saved by pressing the "SET" key, and deleted by pressing the "CLEAR" key.

The indicator circuitry 60, which is electrically connected to the microprocessor and mounted on the wall unit, advances a warning information signal to notify the users of the pollutants found. The indicator circuitry 60 may include sound generating circuitry 92 which includes a sound circuit, a speaker driving circuit and a speaker 61, all electrically connected. The sound circuit stores a sound track, and the speaker driving circuit broadcasts the stored sound track as the warning information signal through the speaker. The warning information may be embodied in musical tones, a synthesized voice, etc. The indicator circuitry may also, or alternatively, include a light generating circuit 97. If included, the light generating circuit 97 may be separate from the sound circuitry 92, or incorporated therein.

The present invention may also include a programmed shell script built into the wall unit aid programmed (hard-coded) with the IP address of the CMS ill order to map an EDI file and send information over the network, and onward to the CMS to be uploaded unto the website, etc.

The present invention is also directed to a method for using a computer to facilitate an order between a buyer and a vendor, in which the buyer inputs into the computer a payment identifier specifying a credit card account or other method of payment.

The present invention further includes an apparatus for facilitating an order for at least one of a plurality of water-contaminant options. The apparatus includes a storage device with a processor connected thereto, the storage device storing a program for controlling the processor, and the processor operative with the program to receive an order and a payment ID specifying a credit card account. The processor is further operative with the program to determine if a predetermined dollar amount is available in the credit card account, as input by the buyer, and includes a validation program to scrutinize customer requests.

Referring in more detail to FIG. 1, a schematic diagram of a system for monitoring the quality of water in a home, office or industrial setting, in accordance with the principles of the present invention, is provided. In general, the preferred system comprises a detecting unit 1000 having a detection device 30 with an optional halocarbons in chlorine analyzer 20 where the incoming liquid is converted into gas. Alternatively or additionally, the detecting unit 1000 may have a UV lamp/reactor 25 and/or a chromatographic column 40. Whether one, two or all three of the UV lamp 25, chlorine analyzer 20 and column 40 are included depends upon the user's requirements, i.e., which contaminants the user wishes to have monitored. As used herein, "contaminants" refers to heavy metals, impurities, or any other component of the water which is desired to be monitored, with chlorine being a primary example. Sulfur, nitrates and lead also represent potential hazards. Lead is generally only present in drinking water as a result of corrosion of lead solder, lead-containing brass fittings, or lead pipes which are located close to or in domestic plumbing and the service connections to buildings. Lead ingestion, which can cause a number of neurological disorders, is particularly dangerous to pregnant women (the fetus) and young children. Representatively, the limit for lead in Ontario, Canada is 10 ug/L.

In typical operation, the water stream runs firstly through the chlorine analyzer. then onward to the ultra-violet lamp, and lastly through to the chromatographic column. Alternatively, three separate water lines may be used, running in parallel to each device, respectively. The detecting unit 1000 may be an ultraviolet detection analyzer device, set at 210–290 nanometers, for example, which may be located under the sink area in a kitchen, adjacent the hot water heater or a pump in a basement or utility room, or related environment. With this arrangement, the analysis cycle would be about 400 seconds, providing a sufficient period of time after which all components of the sample will have passed through the detector for the fluid to purge the chromatographic column 40 and detection device 30 before the next sample is received. The detector then ionizes the separated chemical $H_2O$ components therein, eluting from the chromatographic column 40 and entering the detector from the stream.

The ionized components collect at a collector plate 111 in the chromatographic column 40 of the detecting unit 1000, shown in FIG. 2. Additional collector plates 111 may be mounted in the column 40, at either or both ends thereof. Alternatively, electrodes may be used as appropriate or desired. A current is generated proportional to and commensurate with the amount of the individual components being detected. Representative specifications for the chromatographic column are as follows: 0.32-mm ID×30 m fused silica capillary, 1 um DB-5 (or equivalent) at linear velocity of 20 cm/s; temperature program of 35° C. for 5 min, ramp 10° C./min to 70° C., then 20° C./min to 200° C. Note that heavy metals typically take longer to make it through the column, leading to the possibility that bio-fouling may occur. Maintenance cleaning is therefore recommended on a regular basis, e.g., every six months.

The detection device 30 may be embodied as any standard, commercially available, ultraviolet detector such as, for example, the detector made by ISCO INC. Other suitable detectors may, of course, be used. The detector typically includes electrodes in contact with the incoming water stream in order to obtain comparative conductivity readings from the intermittent tap water inflow and may include, as already noted, an optional ultraviolet detector 25. The ultraviolet lamp/reactor 25 and the chlorine analyzer may be directly connected to the detection device 30. FIG. 3 shows the UV lamp/reactor 25, having an elongated outlet 6 mounted at the upper end thereof. An outlet housing 2 in coaxial relationship with the elongated outlet fitting and rotatable about an axis of the fitting, includes a radial spout 7 affixed to the bottom end of the apparatus for use in water drainage into a sink or pipe system. Rheodine valves may also be used, running from line to line, if necessary.

As shown in FIGS. 1 and 3, the detector passes an ultraviolet light through the sample passing through the chamber 3 of the reactor 25. The ultraviolet light is then absorbed by the ions, causing the excitation thereof. By means of certain pre-amplifiers, a current flow 4 is generated. This current 5 is proportional to the amount of ions present. The current signal, coming from a pre-amplifier voltage reading, is transmitted to the microprocessor which converts the signal using signal converter 94 to a readable form indicative of the contents present in the sample.

The column 40 includes a standard sampling valve 110 which may be embodied as a 6-port sample injection with two heavy arcs representing the connecting passages in the rotor seal. Within the rotor of the valve is an inlet port which is moveable. The sampling valve may be (pneumatically) actuated and controlled by using a 4-way solenoid-actuated valve, which would be electrically wired to the control box unit 50 located on an adjacent wall. A Valco switching valve may also be used as an alternative embodiment. A moveable slider plate with two grooves can also be used between the two positions of the valve: deactive and active (water injection). This valve arrangement allows the loading of the sample loop and injection into the chromatographic column 40 through a port One such suitable column would be the one manufactured by Dionex. This setup represents a type of Ion Selective Electrode Chromatography (ISE).

At any given point in time after the sample has been carried from the sample loop by the carrier system to the chromatographic column 40, the valve 10 is actuated in response to a command from the microprocessor 50 back into its de-active position, permitting the sample from the incoming stream line to flow through the sample loop ready for the next analysis.

Figure 4A:
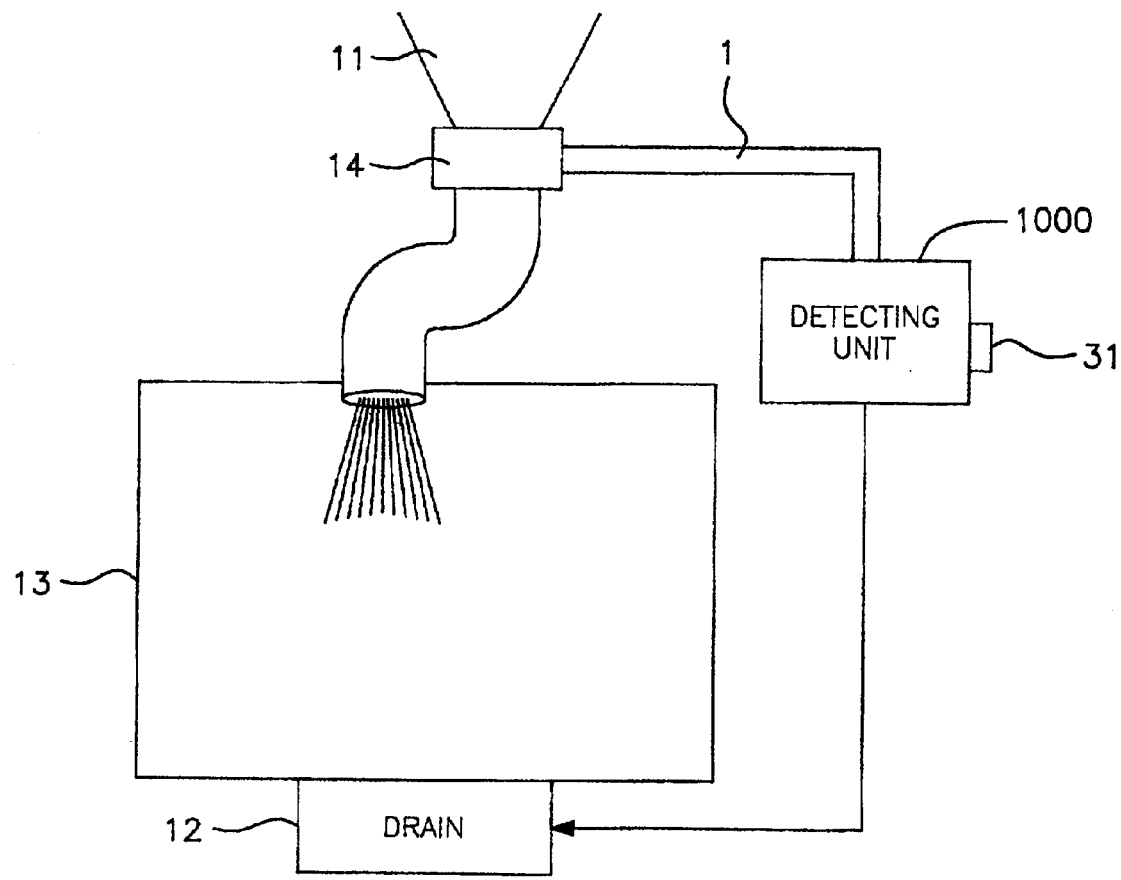
FIG. 4A is a drawing of the detecting unit of the present invention according to one embodiment, in combination with residential plumbing.
Figure 4B:
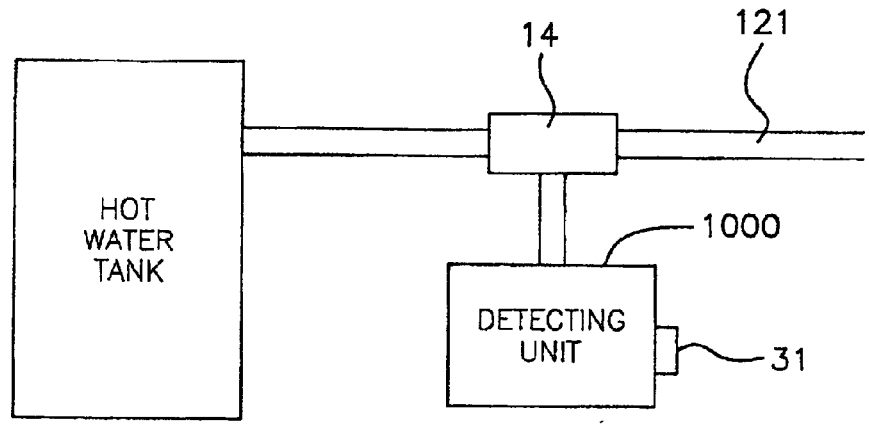
FIG. 4B is a drawing of the detecting unit of the present invention according to a second embodiment, in combination with residential plumbing.

As shown in FIGS. 4A and 4B, the apparatus of the present invention preferably includes an "ON" switch 31 which is used to start the water monitoring process and electrically signal the battery 30A and wall unit 2000 into operation. In the embodiment shown in FIG. 4A, the detecting unit 1000 may be conveniently coupled to a diverter valve 14 which, in turn, is connected to the sink water faucet 11. The diverter valve may be manually set for water flow from the faucet 11 into the sink 13 when it is in a first position, and for water flow through the stream-line 1 of the invention when it is in a second position. Valves can be flipped over for calibration to flow-through cells as well. Usually, the detecting unit of the invention is coupled to the diverter 14 through an angled elbow which is fitted into the inlet of the detecting unit at its upper end for 360 degree rotational movement. The older ORION units may be used, with a running calibration. This also permits placement of the unit in either the lower left or right side of the sink with a minimum length of connecting tubing.

The detector unit is further equipped with a pressure balanced 360 degree rotatable outlet housing, with an elongated spout 7 being fitted into the outlet housing. The sample exits the detector through an output line to a vent stream, and onward into the sink drainage system 12. Incidentally, by way of example, in the embodiment of FIGS. 2, 3 and 4A, and 4B, all the components, including the lines and valves, etc. should preferably be fabricated from chlorine resistant materials such as Kel-F plastic and/or metals like nickel.

FIG. 4B illustrates a second preferred embodiment of the present invention as integrated in a household setting. The detecting unit 1000 is installed adjacent an incoming water line 121 through a diverter valve 14. This installation would most logically be incorporated with the hot water heater or other device where the water, after being analyzed, can share existing drain facilities. The detecting unit 1000 would therefore most typically be in the basement, utility room, or similar location, while the monitoring unit is in one of the living spaces within the residence for receipt of alarm notification.

As an additional mode of operation of the detecting unit, the water may be forced with rapid linear velocity along a shallow helical path close to the ultra-violet (UV) source for exposure to the UV light 25, with the water being heated and mixed at this rapid velocity and in close proximity to the ultraviolet light source. The liquid increases its linear speed to pass through the narrow helical passageway thus creating further turbulence, forcing the liquid closely against the ultraviolet lamp 25 and increasing its path length along the helix to cause high intensity radiation with the ultraviolet light and mixing for reaction. The UV lamp/reactor 25 then repeats this process until the heavier metals are oxidized as the water moves vertically upwardly along a single UV lamp to the top, where the minerals flow into the detection device 30 for detection, measuring and finally transmission, in order to report and record as discussed above. Elements converted to the gas phase can also be detected in that phase by means of an infrared detector, such as sulfur, iron, nitrates, lead, etc. What is described here is, in effect, a UV absorbent spectrometer, tuned to the appropriate calibration (incorporating a data-array sensor).

If the only contaminant to be tested for is chlorine, a fiber-optic based residual chlorine monitor, using a sensor/transduction-based system, may be used. Spectroscopy is an analytical field with a range of uses, from identification of materials, to quantization of certain optical properties. Spectroscopic measurements are generally taken in relatively narrow spectral regions, for instance, Ultraviolet-Visible-Near Infrared (UV-VIS-NIR) from 170 nm to 2.5 u, and Infrared (IR) from 2.5 u to 25 u. Several varieties of sensing mechanisms are mechanisms are being developed to that end.

Based on differential absorption concepts in spectroscopy, the chlorine-only device utilizes a novel miniature monolithic diode array spectrometer operating in the UV and visible (UV-Vis) region of the spectrum in combination with an optical flow-through cell of length 430 mm. A computer controlled deuteriun lamp source may be used. The specifications of the sensor are as follows: limit of 0.2 mg 1  minus 1 of free chlorine in water, relying on the fact that the OC1* minus ion, in which form dissolved chlorine exists at high pH (greater than 9), strongly absorbs light at 290 nm. This device has been shown to be able to measure concentrations lower than 1 ppm, while representative drinking water regulations require that a sensor be able to detect between 0.2 mg/L to 4.0 mg/L chlorine for our communities.

In this and other similar modes of the present invention, a calculator and water flowmeter can be installed to generate a series of pulse waves which are transmitted to the calculator when the water stream is actuated by means of the aforementioned valve system. The calculator, which may be embodied as the microprocessor 50, receives and accumulates such pulse waves to determine an electric current value as a condition detecting signal. Then, when the pollution condition detecting value generated by this operational amplifier is larger than the predetermined reference value preset in the operational amplifier, the microprocessor activates the sound generating circuitry 92 of the indicator circuitry to generate a musical or other distinctive warning sound to notify the users that the impurity of the water elements is at a high and unsafe level.

Accordingly, as a result of this unsafe condition the microprocessor is programmed to then transmit an activated signal to the CMS 4000 with all these inherent values. In this way monitoring of water quality can be assured on an ongoing and immediate basis. By contrast, test readings are not taken during periods of operation at a performance level which is less than optimum, such as immediately after tap water flow is resumed to the system following an extended off period.

The wall unit 2000 translates the data for output onto the network 3000 using a transmission circuit 70, and may be similar to the security control box that is seen on many home alarm systems. The microprocessor 50 controls the overall operations of the monitoring system and electronic data interface (EDI) connectivity. All detected values are temporarily stored in the wall unit 2000 and upon pushing the user controlled "SEND" button 80, are sent by transmission circuitry 70 via the network to the off-site CMS 4000.

The CMS 4000 receives input from the individual components of the detection unit and translates that input back into suitable data which is permanently stored on a database where it can be charted, and sent to the user at his/her request. The station may comprise a computer, a monitor, a keyboard and an output device such as a printer, all of which are typically located in another geographic location. Users can sign up virtually instantaneously for the water monitoring service through the CMS 4000, via the website and interface 5000. Information is transmitted via electronic data interface (EDI) standard formats, such as the File Transfer Protocol (FTP) commonly used for the Internet, and one CMS can provide monitoring for thousands of users in one geographical region. In the preferred embodiment, the CMS includes a central controller 100, user interface 200, and associated databases 300. The CMS system also receives various types of customer orders, assumes payment and subsequently verifies, records and outputs data to screen and print output 400.

Due to the different natures and configurations of the general apparatus', i.e., the detector, monitor and control box, various water quality determining methods can be applied. Potentially harmful minerals such as iron, lead, and ethylene may also be detected.

Referring in more detail to FIG. 6, a block diagram of the wall unit monitoring device 2000 of the present invention is provided. The wall unit comprises a microprocessor 50, sound circuitry 92 electrically connected to the microprocessor and to speaker 61, signal converter 94, transmission circuit 70, power source 96, input device 99, light generating circuit 97, and input/output (I/O) memory and signal sensor 98. The I/O memory 98 is preferably embodied using a monolithic chip, and the programs stored therein control the entire operation of the monitoring device on the wall unit. Other memory configurations may also be used.

In terms of system architecture and FIG. 5, each node is connected via an Internet connection using a public switched phone network, such as provided by a local or regional telephone operating company. Connection may also be provided by dedicated data lines, cellular, Personal Communication Systems (PCS), microwave, or satellite networks, etc. A conventional server with sufficient memory and processing capability may be used as central controller 100. In one embodiment the central controller operates as a web server, receiving orders generated by customers. The central controller must be capable of processing high volume transactions, and processing communications and database searches. Data storage devices may include hard disk magnetic or optical storage units. These devices contain databases 300 used in the processing of orders and incoming values, including a customer database, payment database, contract database, pollutant detection database, and audit database 300. ORACLE software can be used to create and maintain these databases. Known operating systems, such as Unix, may be used to interface between the databases 300 and the central controller 100.

The customer database maintains data on users with fields such as name, address, credit card number, phone number, ID number, email address, credit history, past system usage, public/private key info, etc. This information is obtained when the user first registers with the system.

The pollutant detection database tracks all incoming impurity detection values with fields such as status, tracking number, date, time, element(s), etc. An audit database simply stores file transfer and error information relating to the values per user, allowing it to be retrieved for later analysis.

FIG. 7 illustrates how the overall connectivity works from the outset to the microprocessor in the wall unit to the network and central monitoring station to the website interactive operability. In the preferred embodiment, all this information can be accessed at any time on-line at a special protected website 5000 set up for the users for that purpose. The detecting unit 1000 shown converts raw signals indicating a condition of activated impurities detected by the system concerning water quality into an analog file with conditional data that is converted by converter 35 and sent electronically via wiring to the microprocessor wall unit 2000 where it is translated and mapped into a digital flat-file format using signal converter 94. From there, it is transmitted, in response to depression of the "SEND" button 80, via the network 3000 to the Central Monitoring Station 4000 by use of a programmed IP address, which is the CMS FTP-server site. From there, it is mapped back into the EDI format and imported into a computer screen where details of chlorine and other contaminants are output.

The programming language SAS (v8.1) may be used to provide the subsystem to upload the FTP file from the common data acquisition network. The data is then sorted into selective screens as appropriate, e.g., one for pH and chlorine values, one for heavy metals, etc. A table is referenced with data that corresponds to the coded values that were transmitted to the CMS 4000. Any calculations would also be performed there, along with error-handling, reports, etc. SAS provides data access management, analysis and data presentation, as well as data-warehouse mining capabilities. Other programming languages and configurations may also be used, e.g., SQL, as would be known by persons of ordinary skill in the art.

Prior to implementation of the system, formatting of specific chlorine and other data for each of the elements of the drinking water detection system are input, through input device 99, shown in FIG. 6, and into the microprocessor 50, as respective predetermined reference values. The detecting unit 1000, however configured with UV, chlorine analyzer, or fiber-optic based residual chlorine monitor, etc, then monitors the tap water condition for contaminants, as desired and configured. This generates a quality detecting value regarding the water elements by the detecting device. The quality detecting value is then compared with the respective predetermined reference value regarding the germ life, for example, of each of the chlorine and mineral elements inherent in the tap water stream. A digital signal is sent to the microprocessor when a condition detecting value of one of the elements is detected that is approximate to the respective predetermined reference value, indicating that that element has reached an unsafe level. Thereafter, an activation signal is sent to the indicator circuitry, which is electrically connected to the microprocessor, and an informational data feed is sent to the CMS for recording to a database, all via the common data acquisition network 3000.

Figure 8:
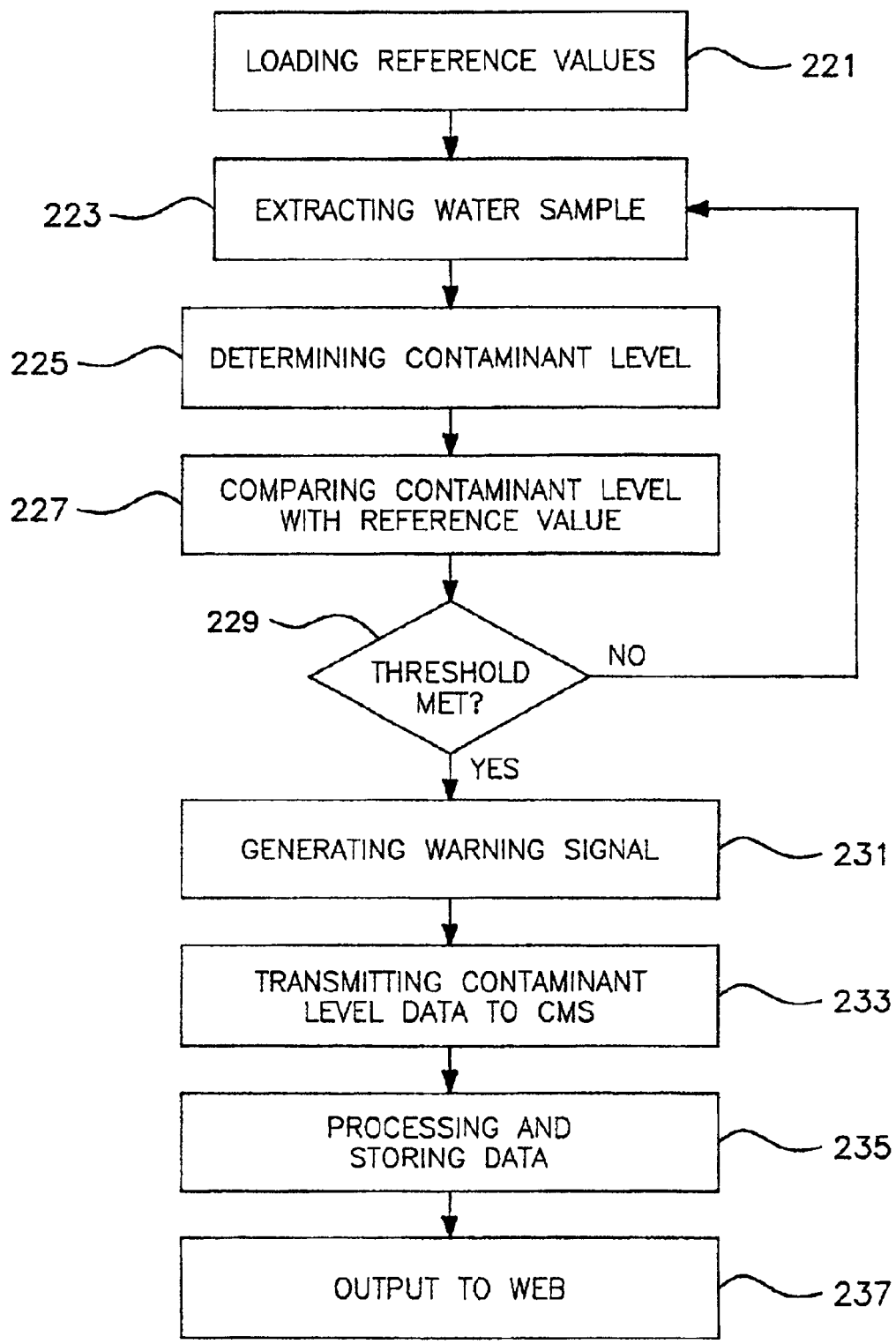
FIG. 8 is a flowchart setting forth the steps undertaken according to the present invention in monitoring water quality measurements over time and reporting in response to contaminant level.

The steps undertaken in setting up and operating the water quality monitoring system and method are broadly depicted in FIGS. 8 and 9. FIG. 8 sets forth the method in which data is forwarded to the CMS whenever a detected contaminant level exceeds a predetermined threshold value. As shown, the method includes the steps of loading reference or threshold values into the microprocessor, step 221, and extracting a water sample, step 223, using the detecting unit. Upon determining a contaminant level, step 225, the contaminant level is compared with the reference or threshold value, step 227. If the contaminant level does not meet the threshold value, step 229, the method proceeds with the extraction of another water sample, step 223, and repeats the subsequent determining and comparing steps. If the contaminant level meets or exceeds the threshold value, step 229, the monitoring unit is notified to generate a warning signal, step 231. The contaminant level data is transmitted to the CMS, step 233, where such data is processed and stored, step 235. The data is thereafter output to the web, step 237, for distribution to and review by the water quality monitoring consumers.

FIG. 9 sets forth the method in which data is forwarded to the CMS whenever a detected contaminant level exceeds a predetermined threshold value or when a predetermined number of water samples have been evaluated. As shown, the method includes the steps of loading reference or threshold values into the microprocessor, step 321, and loading sensor measurement data obtained from standard measurements into the CMS, step 323. Standard measurements are initial measurements taken to establish a baseline of the water quality at a particular consumer's household. Reference data is then compared with sensor measurement data taken from a tap water sample, step 325. The results of the comparison are recorded at the monitoring unit, step 327, and if the comparison shows that the reference threshold value has been met or exceeded, steps 329, the monitoring unit generates a warning signal, step 331, and the data is forwarded to the CMS for recording and trend analysis, step 335. A trend analysis may be derived by comparing water quality measurements taken over time with the initial standard measurements.

If the comparison of the sensor measurement data with the threshold value indicates that the threshold has not been met, step 329, a determination is made as to whether a predetermined number of water samples have been evaluated, step 333. If the sample threshold has not been met, the method returns to compare the reference data with a next set of sensor measurement data, step 325. If the sample threshold has been met, step 333, the recorded data is forwarded to the CMS for recording and trend analysis, step 335. Once the data has been processed and recorded by the CMS, such data is output to the web network, step 337, for distribution to and review by the water quality monitoring consumers.

Depending upon the results of water quality analysis directed to a particular reporting consumer, the CMS may initiate notification of all consumers within a specified range of the reporting consumer of the possibility of a water quality problem. Such notification could be effected through automatic email generation to subscribing consumers. Alternatively, the system could be configured to allow the CMS to communicate directly with the monitoring units to trigger a warning indication on the monitoring units themselves. Through such early notification options, the CMS could perform a proactive role in warning surrounding consumers even before their water is actually degraded. This aspect of the present invention is particularly valuable in those situations in which a water supply may be compromised by deliberate sabotage. Trend data may also indicate to the CMS that a particular problem may be impending, allowing anticipatory action to be undertaken.

The CMS may include a single computer acting as central controller, as has been described in connection with the above embodiments, but those skilled in the art will realize that the functionality can be distributed over a plurality of computer servers. In one embodiment, central controller (CMS) is configured in a distributed architecture wherein the databases and processors are housed in separate units or locations. Each of these controllers is attached to a LAN hub which serves as the primary communication link with the other controllers and interface devices. This hub may have minimal processing capability itself, serving primarily as a communications router. An encrypted router would also be set up outside of the intranet environment to provide added security. An almost unlimited number of controllers may be supported. This particular arrangement yields a more dynamic and flexible system, less prone to catastrophic hardware failures affecting the entire system. The hardware for these servers would be configured similarly to that described for the central controller. All information and products would be made available on the website 5000 for Internet access if users wish to run queries on their individual statistics. This site is preferably password protected for inquiries, but available to any prospective users for e-tail sales, marketing, etc.

This is essentially a buyer-driven system in which the customer transmits payment for installation and services through a live interactive website interface. The system according to the present invention yields certain benefits and efficiencies not available in the prior art. Customers can exercise more control over the terms and conditions of their contract, including start and expiry dates. Currently there is no such transmission system that allows the customer such flexibility and enhanced processing power and speed.

The steps undertaken to establish the method of collecting data from a plurality of residential water monitoring systems are representatively set forth in FIG. 10. The process begins with the CMS signing up consumers through the web site interface, step 441, and establishing a data communication line with each participating consumer, step 443. Installation of the detecting and monitoring units may be completed by a third party contracting company such as those who install residential alarm systems. Once the consumers are registered with the CMS, the CMS receives water contaminant data from each of such consumers, step 445, on an automated basis from the consumer's monitoring unit, as already discussed in connection with FIGS. 8 and 9. The data is processed and stored, step 447, and output to the web site, step 449, for consumer access and review. The CMS may also generate reports, step 451, to be distributed to particular consumers summarizing their water quality data. Reports may be generated automatically or in response to specific consumer request.

By virtue of the above described system and analyzers, there is provided an effective means for determining the quality of tap water for users in a more immediate fashion. The system provides for the on-line detection and measurement of the significant contaminants which may be present in the water. The analyzer 20 is capable of detecting and measuring low concentrations of respective contaminants with precision and accuracy, and the system provides a means for providing and recording of informational data regarding the quality of the water on a real time basis to the CMS via a distributed computer network. The system allows for valid comparison of data collected in different places at various times, and identification of trends in water quality. The new availability of reliable, up-to-date information on contaminants to which the public may be exposed is essential for establishing new standards/objectives or revising the current ones, especially regarding certain heavy-metals such as lead or zinc.

With the advent of new technologies, new business methods expand and therefore challenge traditional contract principles. Thus some legal issues in the field of electronic commerce still remain unresolved. Despite this uncertainty however, when an exchange occurs in a purely electronic environment the threshold legal determination revolves around whether the electronic messages establish an acceptance of the data provided given the absence of documentation in the case of EDI. Users subscribe directly to this service for installation, etc., and typically pay a one-time only installation fee along with a nominal monitoring fee per month, depending on what degree of detection analysis is subscribed to. Specialized reports directed to a particular analysis may also be requested for an additional fee. For example, a consumer could request water quality results obtained from consumers in a particular geographical area, with or without a comparison to their own water quality data. Water quality data could be presented historically to identify trends in a given area or across several areas. Such information is valuable not only empirically but also for the consumer's peace of mind, particularly in today's climate when the real possibility exists that contaminants may be introduced deliberately for social and political ends.

The present invention plays an essential role in ensuring the purity of the water we drink. While today's drinking water regulations say that we must monitor at the industrial plant level, water quality can deteriorate between the plant and the customer's tap. Pipe size also influences chlorine decay, especially in warm water, and numerous factors affect water quality in the distribution system. Samples taken at the consumer's taps provide the greatest assurance about delivered water quality. The present invention is a valuable line of defense, providing a warning system that is engineered to fit right into the home.

Thus, the objects stated in the beginning are attained. While the invention as described above has reference to specific embodiments thereof, it is apparent that many changes, modifications and variations can be made without departing from the concept disclosed herein. Accordingly, it is intended to embrace all such changes, modifications and variations that fall within the spirit and broad scope of the appended claims.

I claim:

1. A water quality monitoring and transmission system comprising:
  a detecting unit having a water sensor adapted for use in a household environment to detect contaminants in running water, said water sensor including an ultraviolet lamp and reactor;
  a monitoring unit located proximate and electrically connected to said detecting unit for receiving contaminant level data therefrom;
  a central monitoring station, remotely located from said detecting unit and said monitoring unit, said central monitoring station in communication with said monitoring unit through a communication channel over a distributed computer network.

2. The water quality monitoring and transmission system as set forth in claim 1, wherein said detecting unit further includes an amplifier coupled to said water sensor and having a predetermined reference value for comparison with said contaminant level, and an analog to digital converter coupled to said amplifier for transmitting a digital signal to said monitoring unit in response to said contaminant level exceeding said predetermined reference value.

3. The water quality monitoring and transmission system as set forth in claim 2, wherein said water sensor further includes a chlorine analyzer and a chromatographic column for analyzing water contaminant levels in said running water.

4. The water quality monitoring and transmission system as set forth in claim 3, wherein said monitoring unit includes indicator circuitry for generating a warning signal detectable in said household environment in response to receipt of said digital signal.

5. The water quality monitoring and transmission system as set forth in claim 1, wherein said detecting unit includes a shallow helical path close to said ultraviolet lamp along which water is forced with rapid linear velocity to create high intensity radiation with the ultraviolet light.

6. The water quality monitoring and transmission system as set forth in claim 1, wherein said detecting unit further includes a fiber-optic based residual chlorine monitor.

7. The water quality monitoring and transmission system as set forth in claim 1, wherein said detecting unit is sized to fit in a compact area in said household environment and further includes at least one of a chlorine analyzer and a chromatographic column for analyzing chlorine levels in said running water.

8. The water quality monitoring and transmission system as set forth in claim 1, wherein said monitoring unit comprises:
  a microprocessor, electrically connected to said detecting unit, for controlling said monitoring unit and said detecting unit;
  indicator circuitry, electrically connected to and controlled by said microprocessor, for generating a warning signal; and
  a transmission circuit, electrically connected to and controlled by said microprocessor, for transmitting data to said central monitoring unit over said communication channel;
  said monitoring system being wall-mounted in said household environment.

9. The water quality monitoring and transmission system as set forth in claim 8, wherein said monitoring unit further comprises data input circuitry, electrically connected to said microprocessor, for inputting predetermined reference values into said microprocessor.

10. The water quality monitoring and transmission system as set forth in claim 8, wherein said indicator circuitry includes sound generating circuitry for generating an auditory warning signal.

11. The water quality monitoring and transmission system as set forth in claim 8, wherein said indicator circuitry includes light generating circuitry for generating a visual warning signal.

12. The water quality monitoring and transmission system as set forth in claim 8, wherein said monitoring unit includes a programmed shell script programmed with an address of said central monitoring station to map an EDI file and send data over said communication channel.

13. The water quality monitoring and transmission system as set forth in claim 1, wherein said central monitoring station includes a central controller and a plurality of databases, said central monitoring station tracking water contaminant data received from a plurality of household monitoring units, and visually presenting said data on a dynamic basis using the distributed computer network.

14. The water quality monitoring and transmission system as set forth in claim 13, wherein said distributed computer network is the Internet and said central monitoring station includes a web site through which information is made available to and collected from consumers.

15. A water quality monitoring and transmission system comprising:
  a detecting unit having a water sensor with an ultraviolet lamp/reactor for detecting a contaminant level in a sample of running water, said detecting unit transmitting a signal when said contaminant level exceeds a predetermined threshold;
  a monitoring unit located proximate and electrically connected to said detecting unit, said monitoring unit receiving said signal from said detecting unit and generating a warning signal indicating unsafe water quality;

a central monitoring station, remotely located from said detecting unit and said monitoring unit, said central monitoring station in communication with said monitoring unit over a distributed computer network;

said monitoring unit including a transmission circuit for transmitting said contaminant level to said central monitoring station for processing and storage, said central monitoring station presenting a plurality of water quality data received from a plurality of monitoring units on a web site accessible through the distributed computer network.

16. The water quality monitoring and transmission system as set forth in claim 15, wherein said detecting unit further includes at least one of a chlorine analyzer and a chromatographic column for analyzing water contaminant levels in said running water.

17. The water quality monitoring and transmission system as set forth in claim 15, wherein said detecting unit further includes an amplifier coupled to said water sensor and having a predetermined reference value for comparison with said contaminant level, and an analog to digital voltage converter coupled to said amplifier for transmitting a digital signal to said monitoring unit in response to said contaminant level exceeding said predetermined reference value.

18. The water quality monitoring and transmission system as set forth in claim 17, wherein said water sensor further includes a chlorine analyzer and a chromatographic column for analyzing chlorine levels in said running water.

19. The water quality monitoring and transmission system as set forth in claim 18, wherein said ultraviolet lamp/reactor is set at 210–290 nanometers.

20. The water quality monitoring and transmission system as set forth in claim 17, wherein said monitoring unit includes indicator circuitry for generating said warning signal in response to receipt of said digital signal.

21. The water quality monitoring and transmission system as set forth in claim 15, wherein said detecting unit includes a shallow helical path close to said ultraviolet lamp along which water is forced with rapid linear velocity to create high intensity radiation with the ultraviolet light.

22. The water quality monitoring and transmission system as set forth in claim 15, wherein said detecting unit further includes a fiber-optic based residual chlorine monitor.

23. The water quality monitoring and transmission system as set forth in claim 15, wherein said monitoring unit comprises:

a microprocessor, electrically connected to said detecting unit, for controlling said monitoring unit and said detecting unit; and a transmission circuit, electrically connected to and controlled by said microprocessor, for transmitting data to said central monitoring unit over said distributed computer network;

said monitoring system being wall-mounted in a household environment.

24. The water quality monitoring and transmission system as set forth in claim 23, wherein said monitoring unit further comprises data input circuitry, electrically connected to said microprocessor, for inputting predetermined reference values into said microprocessor.

25. The water quality monitoring and transmission system as set forth in claim 15, wherein said monitoring unit includes sound generating circuitry for generating an auditory warning signal.

26. The water quality monitoring and transmission system as set forth in claim 15, wherein said monitoring unit includes light generating circuitry for generating a visual warning signal.

27. The water quality monitoring and transmission system as set forth in claim 15, wherein said monitoring unit includes a programmed shell script programmed with an address of said central monitoring station to map an EDI file and send data over said distributed computer network.

28. The water quality monitoring and transmission system as set forth in claim 15, wherein said central monitoring station includes a central controller and a plurality of databases, said central monitoring station tracking data received from a plurality of household monitoring units, and visually presenting said data on a dynamic basis using the distributed computer network.

29. The water quality monitoring and transmission system as set forth in claim 28, wherein said distributed computer network is the Internet and said central monitoring station includes a web site through which information is made available to and collected from consumers.

30. A method of monitoring water quality in a household setting, comprising the steps of:

extracting a water sample from running tap water using a fiber-optic based residual chlorine monitor in combination with an optical flow-through cell and a controlled lamp source as a detecting unit installed in a household environment;

determining a contaminant level in said water sample using said detecting unit by passing ultraviolet light through the water sample to irradiate said water sample and generate, through use of pre-amplifiers, a current proportional to a number of ions absorbing and being excited by said ultraviolet light, said current indicating the contaminant level within said water sample;

comparing, by said detecting unit, said contaminant level with a predetermined reference value;

transmitting, in response to said contaminant level exceeding said reference value, a digital signal to a monitoring unit installed in said household environment;

generating, by said monitoring unit, a warning indicator detectable within said household environment; and transmitting, by said monitoring unit, said contaminant level to a remotely located central monitoring station (CMS) over a distributed computer network.

31. The method as set forth in claim 30, wherein said step of transmitting by said monitoring unit is user-initiated.

32. The method as set forth in claim 30, wherein said step of extracting a water sample is user-initiated.

33. The method as set forth in claim 30, further comprising the step of inputting said predetermined reference value into said monitoring unit using a keypad.

34. The method as set forth in claim 30, further comprising the step of uploading, by said CMS, contaminant level data from a plurality of detecting units to a publicly-accessible web site.

35. The combination of a water quality monitoring and transmission system and residential plumbing in a household, comprising:

a water access area having an incoming tap water supply stream and a drain area;

a detecting unit mounted adjacent said water access area in said household, a water input to said detecting unit connected to said incoming water supply stream, an output of said detecting unit directing water into said drain area, said detecting unit including a fiber-optic based residual chlorine monitor operating in the ultraviolet and visible region in combination with an optical flow-through cell and a controlled lamp source;

a diverter valve connected to said water input and having a first position for bypassing said detecting unit and a second position for directing a sample of flowing tap water into said detecting unit;

a user-actuated switch for toggling between said first and second positions, incoming tap water flowing directly into said water access area and through said drain area when said diverter valve is in the first position and, when said diverter valve is in said second position, a sample of said tap water flowing into said detecting unit for analysis before passing to said water access area and drain area;

a wall-mounted monitoring unit located proximate and electrically connected to said detecting unit, said monitoring unit receiving a signal from said detecting unit indicating a contaminant level and generating a warning signal indicating unsafe water quality which is detectable in said household; and a central monitoring station, remotely located from said detecting unit and said monitoring unit, said central monitoring station in communication with said monitoring unit over a distributed computer network.

36. The water quality monitoring and transmission system as set forth in claim 35, wherein said detecting unit has a detection limit of 0.2 mg 1 (minus 1) of free chlorine in water relying upon strong light absorption of chlorine at 290 nm.

37. The water quality monitoring and transmission system as set forth in claim 36, wherein said monitoring unit includes a transmission circuit for transmitting said contamninant level to said central monitoring station for processing and storage, said central monitoring station presenting a plurality of water quality data received from a plurality of monitoring units on a web site accessible through the distributed computer network.

38. The water quality monitoring and transmission system as set forth in claim 35, wherein said detecting unit includes at least one pure water electrode in contact with said tap water stream to take a conductivity reading representative of general water quality.

39. The water quality monitoring and transmission system as set forth in claim 35, wherein said controlled lamp source is a deuterium lamp source.

40. The water quality monitoring and transmission system as set forth in claim 35, wherein the detecting unit includes a miniature monolithic diode array spectrometer.

41. The water quality monitoring and transmission system as set forth in claim 40, wherein said flow-through cell has a length of approximately 430 mm.

42. The water quality monitoring and transmission system as set forth in claim 35, wherein said water access area is a sink.

* * * * *